(12) United States Patent
Bruder et al.

(10) Patent No.: US 7,215,805 B2
(45) Date of Patent: May 8, 2007

(54) METHOD AND APPARATUS FOR SPIRAL SCAN COMPUTED TOMOGRAPHY

(75) Inventors: Herbert Bruder, Hoechstadt (DE); Thomas Flohr, Uehlfeld (DE); Marc Kachelriess, Nuremberg (DE); Stefan Schaller, Fuerth (DE); Karl Stierstorfer, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 381 days.

(21) Appl. No.: 10/074,145

(22) Filed: Feb. 12, 2002

(65) Prior Publication Data

US 2002/0141628 A1    Oct. 3, 2002

(30) Foreign Application Priority Data

Feb. 12, 2001   (DE) ................ 101 06 398
May 31, 2001   (DE) ................ 101 26 638

(51) Int. Cl.
*G06K 9/00*   (2006.01)

(52) U.S. Cl. .................. 382/131; 378/4; 378/98.6; 378/901

(58) Field of Classification Search ............. 382/128, 382/129, 130, 131, 132, 133, 134; 378/4, 378/15, 19, 21–27, 901, 46, 90, 92, 101, 378/140, 98.4, 98.6, 98.9; 600/425; 250/363.04, 250/370.09
See application file for complete search history.

(56) References Cited

U.S. PATENT DOCUMENTS

| | | | | |
|---|---|---|---|---|
| 5,408,511 A * | 4/1995 | Grangeat et al. | ............. | 378/19 |
| 5,625,660 A * | 4/1997 | Tuy | ............. | 378/15 |
| 5,802,134 A * | 9/1998 | Larson et al. | ............. | 378/4 |
| 6,178,220 B1 * | 1/2001 | Freundlich et al. | ............. | 378/4 |
| 6,408,044 B2 * | 6/2002 | Sembritzki et al. | ............. | 378/15 |
| 6,426,987 B2 * | 7/2002 | Nakamura et al. | ............. | 378/4 |
| 6,504,892 B1 * | 1/2003 | Ning | ............. | 378/4 |

\* cited by examiner

*Primary Examiner*—Jingge Wu
*Assistant Examiner*—Abolfazl Tabatabai
(74) *Attorney, Agent, or Firm*—Schiff Hardin LLP

(57) ABSTRACT

In a method for computed tomography and a computed tomography apparatus for scanning a subject with a conical ray beam emanating from a focus that detects a matrix-like detector array, the focus is moved relative to the subject on a spiral path around a system axis, and the detector array supplies output data corresponding to the incident radiation, and images having an inclined image plane are reconstructed from output data respectively supplied during the movement of the focus on a spiral segment, the image planes of these images are inclined by an inclination angle γ around a first axis intersecting the system axis at a right angle and also are inclined by a tilt angle δ with respect to the system axis around a second axis that intersects the first axis as well as the system axis at a right angle.

34 Claims, 12 Drawing Sheets z-distance/S $R_f \sin \alpha$ [mm]

(mean squared distance)$^{1/2}$ /s $\gamma/\gamma_0$ z-distance/S $R_f \sin \alpha$

METHOD AND APPARATUS FOR SPIRAL SCAN COMPUTED TOMOGRAPHY

BACKGROUND OF THE INVENTION

1. Field of the Invention

The present invention is directed to a method for operating a computed tomography apparatus, and to a computed tomography apparatus, of the type for conducting a spiral scan of an examination subject.

2. Description of the Prior Art

Methods for operating a computed tomography apparatus are known wherein, for scanning a subject with a conical ray beam emanating from a focus which strikes with a matrix-like detector array for detecting the radiation, the focus is moved relative to the subject on a spiral path around a system axis. The detector array supplies output data corresponding to the incident radiation, and images relative to the system axis are reconstructed from the output data respectively supplied during the movement of the focus has each spiral segment. Computed tomography (CT) systems are known having a radiation source with a focus from which a conical ray beam emanates, a matrix-like detector array for detecting the radiation, the detector array supplying output data corresponding to the incident radiation, means for generating a relative motion between the radiation source and the detector array, and the subject, and an image computer to which the output data are supplied. For scanning the subject with the ray beam and the two-dimensional detector array, motion relative to a system axis is generated such that the focus moves relative to the system axis on a helical spiral path whose center axis corresponds to the system axis. The image computer uses the output data respectively supplied during the motion of the focus in spiral segments to reconstruct images having an image plane inclined relative to the system axis.

Such a procedure is referred to as spiral-CT and such a method and CT apparatus are disclosed by U.S. Pat. No. 5,802,134.

The spiral path of the focus F illustrated in FIG. 1 is described by the following equations:

$$\begin{aligned} x_f &= -R_f \cos\alpha \\ y_f &= R_f \sin\alpha \\ z_f &= S \cdot p \cdot \frac{\alpha}{2\pi} \end{aligned} \quad (1)$$

and $$\bar{x} = \begin{pmatrix} -R_f \cos\alpha \\ -R_f \sin\alpha \\ Sp\frac{\alpha}{2\pi} \end{pmatrix}$$

When the detector elements of the detector array are arranged in rows proceeding transversely relative to the system axis Z and in columns proceeding parallel to the system Z, S stands for the extent of a detector row in the direction of the system axis and p stands for the pitch, and $$p = \frac{h}{S}$$

applies, where h stands for the slope of the spiral path per revolution of the focus F. $\alpha$ is the projection angle, and an image plane associated with data that were registered over a projection angle range of $\pm\alpha$ is considered below, with the reference projection belonging to the image plane being at $\alpha_r=0$, i.e. it represents the middle of the projection angle range $\pm\alpha$. Below, $\alpha_r$ is referred to as the reference projection angle.

In conventional spiral-CT, tomograms referred to as transverse tomograms are reconstructed, i.e. images for image planes that reside at a right angle relative to the system axis z and that thus contain the x-axis and y-axis, the x-axis and y-axis being at a right angle relative to one another and to the system axis z.

In the aforementioned U.S. Pat. No. 5,802,134, in contrast, images are reconstructed for image planes that, according to FIG. 2, are inclined by an inclination angle $\gamma$ around the x-axis relative to the system axis z. As a result, the advantage (at least theoretically) is achieved that the images contain fewer artifacts when the inclination angle $\gamma$ is selected such that a good, optimum matching of the image plane to the spiral path is established insofar as possible according to a suitable error criterion, for example minimum square average of the spacing of all points of the spiral segment from the image plane measured in the z-direction.

In U.S. Pat. No. 5,802,134, fan data, i.e. data registered in known fan geometry, are employed for the reconstruction, the data having been acquired with the motion of the focus over a spiral segment having proceeding through a 180° plus the fan angle or cone angle, for example 240°. With respect to the reference projection angle $\alpha_r=0$, the following applies to the normal vector of the image plane:

$$n_{US}(\gamma) = \begin{pmatrix} 0 \\ -\sin\gamma \\ \cos\gamma \end{pmatrix}.$$

The optimum inclination angle $\gamma$ is obviously dependent on the slope of the spirals and thus on the pitch p.

Fundamentally, the method disclosed in U.S. Pat. No. 5,802,134 can be employed for arbitrary values of the pitch p. However, an optimum utilization of the detector area available and thus of the radiation dose applied to the patient for image acquisition (detector and thus dose utilization), is not possible below the maximum pitch $P_{max}$. This is because even though a given transverse slice, i.e. a slice of the subject residing at a right angle relative to the system axis z, is scanned over a spiral segment that is longer than 180° plus the fan or cone angle, only a spiral segment having the length 180° plus the cone angle can be utilized for values of the pitch p below the maximum pitch $P_{max}$, since the utilization of a longer spiral segment would make it impossible to adapt the image plane adequately well to the spiral path.

SUMMARY OF THE INVENTION

An object of the present invention is to provide a method and a CT apparatus of the type initially described wherein the prerequisites for an optimum detector utilization, and thus dose utilization, are established even for values of the pitch p below the maximum pitch $P_{max}$.

This object is achieved according to the invention in a method and CT apparatus wherein images having an inclined image plane are reconstructed from output data respectively supplied during the movement of the focus on a spiral segment, the image planes of these images being inclined by an inclination angle γ around a first axis intersecting the system axis at a right angle and also being inclined by a tilt angle δ with respect to the system axis around a second axis that intersects the first axis as well as the system axis at a right angle.

As a result, it is possible to achieve at least approximately complete detector and dose utilization even given values of the pitch falling below the maximum pitch.

According to a first embodiment of the invention for a given pitch p and a given z-position $z_{ima}$, output data for an overall segment having the length $[-\alpha_{max}, +\alpha_{max}]$ are acquired, with $\alpha_{max}=M\pi/p$ and wherein M is the number of detector rows. This overall segment is subdivided into a number $n_{ima}$ of successfully overlapping spiral segments, each of which having the length of 180° plus cone angle. A separate image with inclined image plane is reconstructed at the location $z_{ima}$ for each of the spiral segments. As a result of the reconstruction of an image having inclined image plane for each of the spiral segments, it is possible—by corresponding selection of the inclination angle γ and of the tilt angle Δ—to optimally adapt the image plane of the image for each of these spiral segments to the corresponding section of the spiral path and to theoretically completely utilize the detector array as well as the dose and to utilize these to the greatest possible extent in practice.

In a second embodiment, $n_{ima}$ images having differently inclined image plane for different z-positions are obtained from the output data acquired for a spiral segment having the length 180° plus cone angle centered with reference to the reference projection angle $\alpha_r=0$. As a result of the reconstruction of a number of images having differently inclined image plane for different z-positions, it is possible—by means of a corresponding selection of inclination angle and of tilt angle Δ—to adapt the image plane of the image optimally to the spiral segment for each of these z-positions and to theoretically completely utilize both the detector array as well as the dose, to the greatest possible extent in practice. In a preferred embodiment of the invention, the number of inclined image planes intersect in a straight line proceeding tangentially relative to the spiral.

In order to obtain an optimally complete detector and dose utilization, the following applies for the extreme values plus $\delta_{max}$ and $-\delta_{max}$ of the tilt angle δ of the inclined image planes belonging to a spiral segment, according to one version of the invention:

$$\pm\delta_{max} = \arctan\left(\frac{-\frac{SM}{2} + Sp\frac{\alpha_l}{2\pi} \pm RFOV\cos\alpha_l\tan\gamma_0}{-\frac{R_f}{\cos\gamma_0} - (\pm RFOV)\frac{\sin\alpha_l}{\cos\gamma_0}}\right)$$

whereby $\gamma_0$ is the value of the inclination angle γ determined according to $$\gamma_0 = \tan\left(\frac{-Sp\hat{\alpha}}{2\pi R_f \sin\hat{\alpha}}\right)$$

for the tile angle δ=0.

For a high image quality, in another version of the invention the appertaining optimum value $\gamma_{min}$ of the inclination angle γ is determined for a given magnitude $|\delta_{max}|$ of the maximum value of the tilt angle δ so that an error criterion, for example minimum square average of the distance of all points of the spiral segment from the image plane measured in z-direction, is met.

When the rotational axis around which the focus rotates, as the symmetry axis, is not identical with the system axis but intersects it at an angle referred to as a gantry angle ρ, then the following applies for the inclination angle γ' to be selected:

$$\gamma' = \arctan\frac{Sp\cdot\cos\rho}{\sqrt{4\pi^2\cdot R_f + S^2 p^2 + 4\pi\cdot R_f\cos\alpha\sin\rho\cdot Sp}}$$

Here as well, there is the possibility of determining the optimum value of the inclination angle γ' for a given magnitude of the maximum value of the tilt angle $|\delta_{max}|$ such that an error criterion, for example minimum average of the distances of all points of the spiral segment from the image plane measured in z-direction, is met.

In order to obtain an optimally complete detector and does utilization, the following also applies according in an embodiment of the invention for $n_{ima}$ of inclined image planes for which images having inclined image plane are generated for each spiral segment:

$$n_{ima} = \text{floor}\left[\frac{sM}{\rho}\right]$$

Likewise for an optimally complete detector and dose utilization, the tilt angles δ of the inclined image planes are determined according to $$\delta(i) = \delta_{max}\frac{2i - (n_{ima} - 1)}{n_{ima} - 1}$$

given the pre-condition of detector rows of equal width.

In order to obtain the transverse tomograms to which users of CT apparatuses are accustomed, a reformatting is provided in an embodiment of the invention, i.e. a transverse tomogram is generated in a further method step by merging a number of images having an inclined image plane. Such merging can ensue by combining a number of images having inclined image plane are combined to form a transverse tomogram by interpolation or by individually weighted average formation.

In a preferred version of the invention, there is the possibility, by merging a number of images with inclined image plane to form a transverse tomogram. The number of images having inclined image plane that are merged for generating a transverse tomogram is selected corresponding to the desired slice thickness of the slices forming the transverse slice. For an optimally high image quality of the transverse tomograms, there is the possibility of reconstructing the images with inclined image plane with the lowest possible slice thickness.

A desired slice thickness of the transverse slice presented in a transverse tomogram can be set in another preferred version of the invention by selecting the number of images having inclined image plane that are combined for generating a transverse tomogram according to $$N_M = 2 \cdot \max(z^*, \sup_\phi \Delta z_R)/S \cdot N_S$$

DESCRIPTION OF THE PREFERRED EMBODIMENTS

Figure 3:
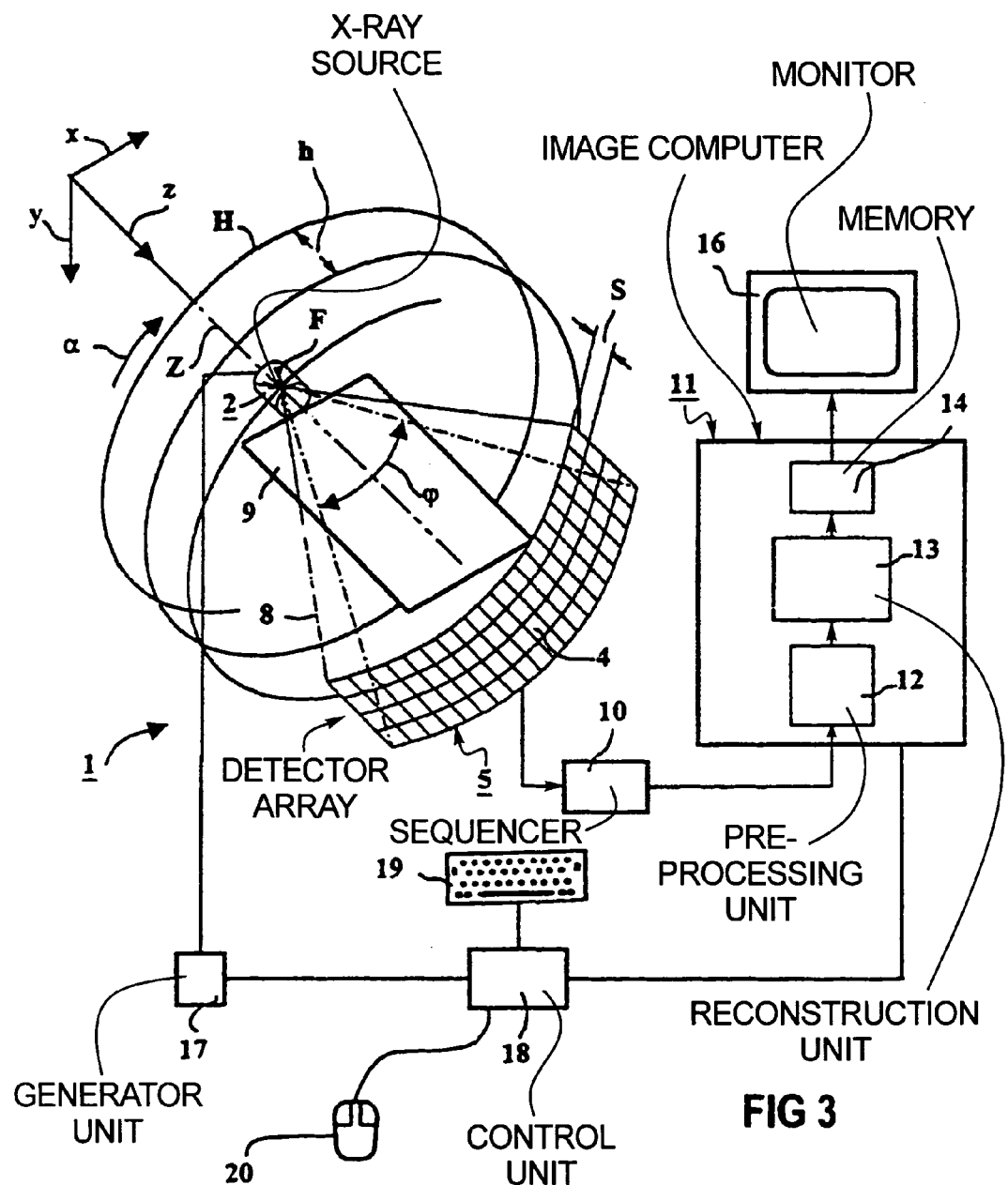
FIGS. 3 and 4 schematically illustrate an inventive CT apparatus operating according to the inventive method.
Figure 4:
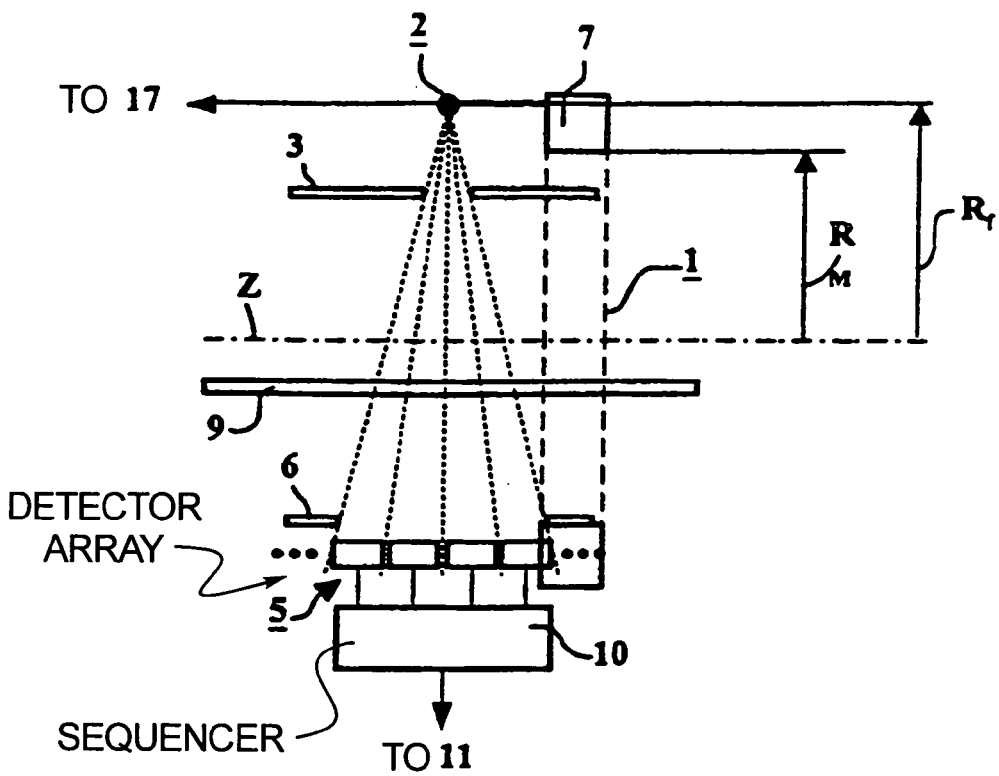

FIGS. 3 and 4 show an inventive multi-slice CT apparatus of the third generation suitable for the implementation of the inventive method. The measurement arrangement 1 thereof has an x-ray source 2 with a source-proximate radiation diaphragm 3 (FIG. 4) and a detector array 5 fashioned as a planar array having a number of rows and columns of detector elements—one of these is referenced 4 in FIG. 3—and having a detector-proximate radiation diaphragm 6 (FIG. 4). The x-ray source 2 with the radiation diaphragm 3 and the detector array 5 with the radiation diaphragm 6 are mounted to a live frame 7 also referred to below as gantry, as shown in FIG. 4. These components are disposed opposite one another such that a pyramidal x-ray beam that emanates from the x-ray source 2 during operation of the CT apparatus, and is gated by the adjustable radiation diaphragm 3 (whose edge rays are referenced 8) is incident onto the detector array 5. The radiation diaphragm 6 is set, with respect to the cross-section of the x-ray beam that is set with the radiation diaphragm 3, so that only that region of the detector array 5 is exposed that can be directly struck by the x-ray beam. In the operating mode illustrated in FIGS. 3 and 4, these are four rows of detector elements. The fact that other rows of detector elements covered by the radiation diaphragm 6 are present is indicated in dotted fashion in FIG. 4.

The x-ray beam exhibits a cone angle φ, which is the aperture angle of the x-ray beam projected into a plane proceeding at a right angle relative to the system axis. The cone angle φ corresponds to the fan angle of the parts of the x-ray beam and the individual rows of the detector array 5.

The gantry 7 can be placed in rotation around the system axis Z by means of a drive device (not shown). The system axis Z coincides with the z-axis of a spatial rectangular coordinate system shown in FIG. 1. The circular opening of the gantry 7 exhibits a radius $R_M$ that corresponds to the radius of the measurement field, or of the object cylinder. The radius on which the focus F moves is referenced $R_f$.

The columns of the detector array 5 likewise proceed in the direction of the z-axis, whereby the rows, whose width S is measured in the direction of the z-axis and amounts, for example to 1 mm, proceed transversely relative to the system axis Z (also the z-axis).

In order to be able to place an examination subject, for example a patient, into the beam path of the x-ray beam, a support mechanism 9 is provided that is displaceable parallel to the system axis Z, i.e. in the direction of the z-axis.

For registering volume data of an examination subject, for example a patient, situated on the support mechanism 9, scanning of the examination subject ensues by registering a number of projections from different projection directions α with movement of the measurement unit1 around the system axis Z. The data supplied by the detector array 5 thus contain a number of projections for each active detector row.

During the continuous rotation of the measuring unit 1 around the system axis Z, the support mechanism 9 is simultaneously continuously displaced in the direction of the system axis Z relative to the measuring unit 1. A synchronization between the rotational movement of the live frame 7 and the translational movement of the support mechanism 9 exists in the sense that the relationship of translational velocity to rotational velocity is constant and this constant relationship can be set by selecting a value for the feed h of the support mechanism 9 per revolution of the live frame 7 that guarantees a complete scanning of the volume of interest of the examination subject.

The relationship of the feed h to the width S of the detector row is, as already mentioned, referred to as pitch p. The maximum pitch $P_{max}$ that just barely assures a gap-free scanning of an examination subject is driven given the pre-condition that all rows of the detector array 5 exhibit the same width S, whereby n is the number of active rows of the detector system 5.

Figure 1:
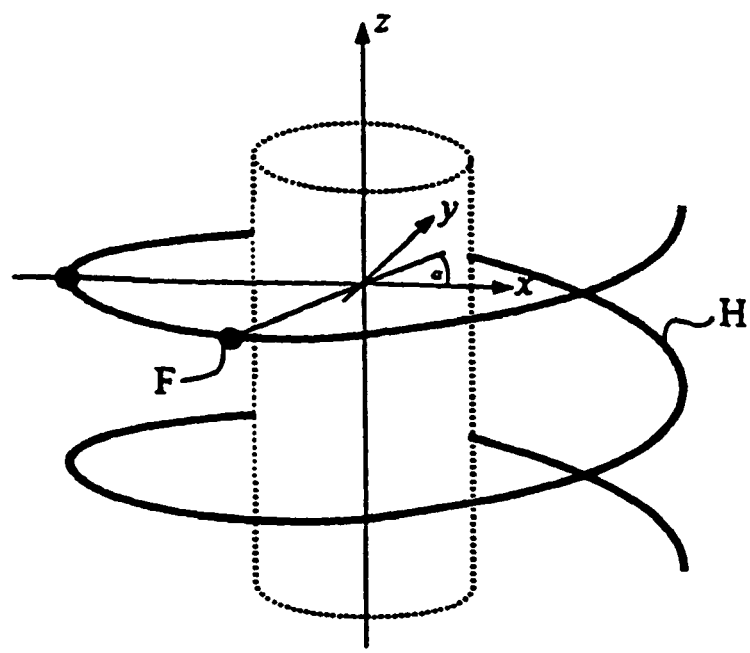
FIGS. 1 and 2 illustrate the geometry of CT methods of the prior art.
Figure 2:
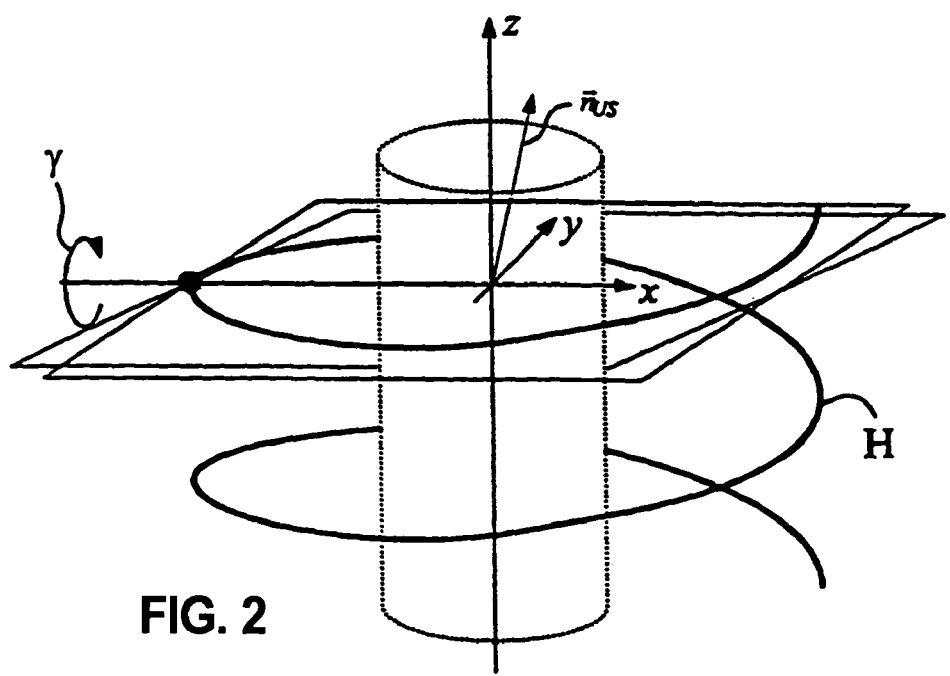

As seen from the examination subject, thus, the focus F of the x-ray source 2 moves around the system axis Z on a helical spiral path referenced H in FIG. 1, for which reason the described type of registration of volume data is also referred to as a spiral scan. The volume data thereby supplied by the detector elements of each row of the detector array 5 (projections respectively allocated to a specific row of the detector array 5 and to a specific position with respect to the system axis Z) are read out in parallel, serialized in a sequencer 10, and transmitted to an image computer 11.

After a pre-processing of the volume data in a pre-processing unit 12 of the image computer 11, the resulting data stream proceeds to a memory 14 wherein the volume data corresponding to the data stream are stored.

The image computer 11 contains a reconstruction unit 13 that uses the volume data to reconstruct image data, for example in the form of tomograms of desired slices of the examination subject, according to methods known to these skilled in the art. The image data reconstructed by the reconstruction unit 13 are stored in a memory 14 and can be displayed as an image on a display unit 16, for example a video monitor, connected to the image computer 11.

The x-ray source 2, for example an x-ray tube, is supplied with the necessary voltages and currents by a generator unit 17. In order to be able to set these to the required values, the generator unit 17 has a control unit 18 with a keyboard 19 and mouse allocated to it that allows the necessary settings.

The rest of the operation and control of the CT apparatus also ensues with the control unit 18 and the keyboard 19 as well as the mouse 20, this being indicated by the control unit 18 being connected to the image computer 11.

In a first operating mode, which corresponds to the usual procedure in spiral scans, transverse tomograms, i.e. tomograms whose image plane proceeds at a right angle relative to the system axis Z, are reconstructed from the volume data registered during the course of a spiral scan according to methods that are known and are described in the literature as 180 LI reconstruction and 360 LI reconstruction.

However, there is also the possibility in a second operating mode of reconstructing tomograms whose image planes are inclined relative to the system axis Z from volume data, at least as an intermediate step.

In contrast to the procedure disclosed by U.S. Pat. No. 5,802,134, one proceeds according to the invention such that the image plane is inclined by an inclination γ and the tilt angle δ with respect to the system axis Z. The inclination γ is around a first axis intersecting the system axis Z at a right angle, namely the x-axis. The tilt angle δ is with respect to the system axis 2 around a second axis, namely the y-axis, both the first axis (x-axis) as well as the system axis Z, as may be seen from FIG. 5.

In a first mode of the second operating mode, output data for a spiral segment having the length $[-\alpha_{max}, +\alpha_{max}]$ are utilized for a given pitch p and a given z-position $z_{ima}$, whereby $\alpha_{max}=M\pi/p$ and M is the number of detector rows, with the z-position indicating the position of the image plane on the z-axis. This overall segment is subdivided into $n_{ima}$ successively overlapping spiral segments, each having the length of 180° plus the cone angle. A separate image having inclined image plane is reconstructed at the location $z_{ima}$ for each of the spiral segments. As a result of the reconstruction of an image with inclined image plane for each of the spiral segments, it is possible—by selection of the inclination angle γ and of the tilt angle δ—to optimally adapt the image plane of the image for each of the spiral segments to the corresponding section of the spiral path, and to theoretically completely utilize the region of the detector array 5 enabled by the radiation diaphragm 6 as well as the radiation dose incident onto this region, and to utilize these in practice to the greatest-region extent.

In a second mode of the second operating mode, a spiral segment having the length 180° plus the cone angle φ centered relative to the reference projection angle $\alpha_r=0$ is utilized, and $n_{ima}$ images having differently inclined image plane for different z-positions are obtained on the basis of this spiral segment. In this mode as well, it is possible—by reconstructing a number of images having differently inclined image plane for different z-positions and by means of a selection of the inclination angle γ and the tilt angle δ—to optimally adapt the image plane of the image for each of these z-positions to the spiral segment and to theoretically completely utilize both the detector array as well as the dose and to utilize these in practice to the farthest-reaching extent. In a preferred embodiment of the invention, the number of inclined image planes thereby intersect in a straight line that proceeds tangentially relative to the spiral.

The second mode is explained in greater detail below.

For simplicity, a single spiral segment shall be considered, this being centered relative to the reference projection angle $\alpha_r=0$. Since the image planes of the $n_{ima}$ images are inclined by the tilt angle δ with respect to the x-axis—by the inclination angle γ—as well as with respect to the y-axis—by the tilt angle δ—the normal vector of an image plane is established by the following:

$$\bar{n}(\gamma, \delta) = \begin{pmatrix} \sin\delta \\ -\cos\delta\sin\gamma \\ \cos\delta\cos\gamma \end{pmatrix}. \quad (2)$$

The distance d (α, δ, γ) that an arbitrary point $(x_f, y_f, z_f)$ on the spiral path exhibits in the z-direction from the image plane inclined by the inclination angle γ and the tilt angle δ is established by the following:

$$d(\alpha, \delta, \gamma) = \bar{n}(\gamma, \delta) \cdot \begin{pmatrix} x_f + R_f \\ y_f \\ z_f \end{pmatrix} = \bar{n}(\gamma, \delta) \cdot \begin{pmatrix} -R_f\cos\alpha + R_f \\ -R_f\sin\alpha \\ Sp\frac{\alpha}{2\pi} \end{pmatrix} = \quad (3)$$

$$= R_f(1 - \cos\alpha)\sin\delta + R_f\sin\alpha\cos\delta\sin\gamma + Sp\frac{\alpha}{2\pi}\cos\delta\cos\gamma$$

It is assumed that the position $(-R_f, 0, 0)$ of the focus F for the reference projection angle $\alpha_r=0$ lies in the image plane.

The inclination angle γ and the tilt angle δ of the inclined image plane must be selected such that the quadratic average of all points on the spiral segment is minimum.

When it is assumed that b-t is the coordinate system x-y rotated around the z-axis by an angle α-π/2, then b-t is the local coordinate system for a projection having the projection angle α.

$$x = b\sin\alpha + t\cos\alpha$$

$$y = -b\cos\alpha + t\sin\alpha \quad (4)$$

When a virtual detector array is imagined that corresponds to the projection of the detector array into a plane containing the system axis z, referred to as the virtual detector plane, then t=0 applies for the detector plane.

Each point (x, y, z) on the image plane is characterized by $$\vec{n}(\gamma,\delta) \cdot \begin{pmatrix} x + R_f \\ y \\ z \end{pmatrix} = (x + R_f)\sin\delta - y\cos\delta\sin\gamma + z\cos\delta\cos\gamma = 0 \quad (5)$$

When (t) with t=0 is introduced into (5), then the intersecting straight line of the virtual detector plane with the image plane is obtained:

$$z(b) = -R_f \frac{\tan\delta}{\cos\gamma} - b\left(\sin\alpha\frac{\tan\delta}{\cos\gamma} + \cos\alpha\tan\gamma\right). \quad (6)$$

The z-coordinate on the virtual detector plane is established by $$z_{Det}(b) = z(b) - Sp\frac{\alpha}{2\pi} = -R_f \frac{\tan\delta}{\cos\gamma} - Sp\frac{\alpha}{2\pi} - b\left(\sin\alpha\frac{\tan\delta}{\cos\gamma} + \cos\alpha\tan\gamma\right). \quad (7)$$

Let the inclination angle γ be initially optimized in the same way as taught by U.S. Pat. No. 5,802,134, i.e. δ=0 for the tilt angle. The following is obtained as a result:

$$\tan\gamma_0 = \frac{-Sp\hat{\alpha}}{2\pi R_f \sin\hat{\alpha}} \quad (8)$$

whereby $\hat{\alpha}$ is the angle at which the spiral path penetrates the image plane. It has been shown that $\hat{\alpha}=\pi/3$ is a beneficial if not optimum value for this parameter.

The tilt angle δ is optimized for the inclination angle $\gamma_0$ obtained according to (8) with $\hat{\alpha}=\pi/3$. The optimization criterion for the tilt angle δ is that the z-coordinate according to (7) for the lines $-RFOV \leq b \leq RFOV$ that limit the region of the examination subject covered by the radiation in the z-direction toward the back or toward the front, must lie not only within the active detector area, i.e. within the region of the detector array 5 enabled by the radiation diaphragm 6 and struck by the radiation, but also must utilize the detector surface optimally well.

For the maximally possible tilt angle $\pm\delta_{max}$, the lines for $b=\pm RFOV$ established by the z-coordinate according to (7) reach the front or back end of the detector area in the z-direction. When this occurs for the respective spiral segment for the projections at the beginning and end of the spiral segment, i.e. for the outermost projection angles $\alpha_i = \pm 120°$, then the following applies:

$$z_{Det}(b = \pm RFOV) = \pm \frac{SM}{2}, \quad (9)$$

whereby M is the number of detector rows and S is the width of the detector row measured in the z-direction.

If equation (6), for $\alpha=\alpha_i$ and $\gamma=\gamma_0$, is inserted into (8) and solved for $\delta_{max}$, the following results:

$$\tan\delta_{max} = \frac{-\frac{SM}{2} + Sp2\frac{\alpha_i}{2\pi} \pm RFOV\cos\alpha_i\tan\gamma_0}{-\frac{R}{\cos\gamma_0} - (\pm RFOV)\frac{\sin\alpha_i}{\cos\gamma_0}}$$

and $$\pm\delta_{max} = \arctan\left(\frac{-\frac{SM}{2} + Sp\frac{\alpha_i}{2\pi} \pm RFOV\cos\alpha_i\tan\gamma_0}{-\frac{R_f}{\cos\gamma_0} - (\pm RFOV)\frac{\sin\alpha_i}{\cos\gamma_0}}\right) \quad (10)$$

A new $\gamma_{min}$ is determined by reiteration for the corresponding $\delta_{max}$, by minimizing the quadratic average of the distances $d(\alpha, \delta_{max}, \gamma)$ measured in the z-direction of all points of the spiral segment from the image plane according to (3).

The available region $[-\delta_{max}, \delta_{max}]$ of the tilt angle is then uniformly subdivided according to the number $n_{ima}$ of the images to be reconstructed with inclined image plane, preferably as in the case of the described exemplary embodiment. In the case of a uniform subdivision, each image plane $0 \leq i \leq n_{ima}-1$ is characterized by the inclination angle $\gamma_{min}$ (that is preferably the same for all image planes, as in the case of the described exemplary embodiment) and by the respective tilt angle $\delta_{(i)}$, whereby the following is valid for the respective tilt angle:

$$\delta(i) = \delta_{max}\frac{2i - (n_{ima} - 1)}{n_{ima} - 1}. \quad (11)$$

The number $n_{ima}$ of the images with inclined image planes to be reconstructed for the spiral segment is established by $$n_{ima} = \text{floor}\left[\frac{SM}{p}\right]. \quad (12)$$

The effect of the inventive method and CT apparatus is described below with reference to the example of a CT apparatus having M=12 detector rows with the width S that is operated with a pitch of p=1 2. A spiral segment having the length $[-\alpha_{max}, \alpha_{max}]$ with $\alpha_{max}=\pi$ is registered for each z-position $z_{ima}$.

Figure 6:
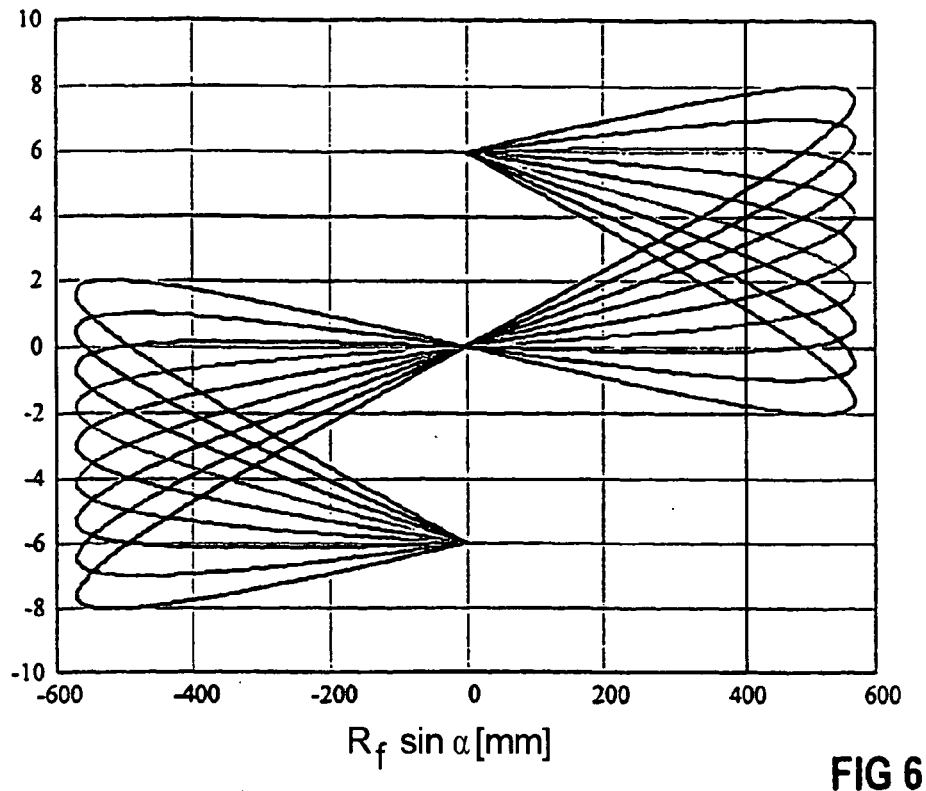
FIG. 6 shows the distances of all points of a spiral segment from the image plane for various inclination angles γ measured in the direction of the z-axis and referenced to the width S of a row of the detector array, over the sine of the projection angle a multiplied by the radius $R_f$, namely for the tilt angle δ=0.

FIG. 6 shows the distances—referenced to the width S of a row of the detector array and measured in the direction of the z-axis—of all points of the spiral segment from the image plane for various inclination angles γ over the sine of the projection angle a multiplied by the radius $R_f$, namely for the tilt angle δ=0.

Figure 7:
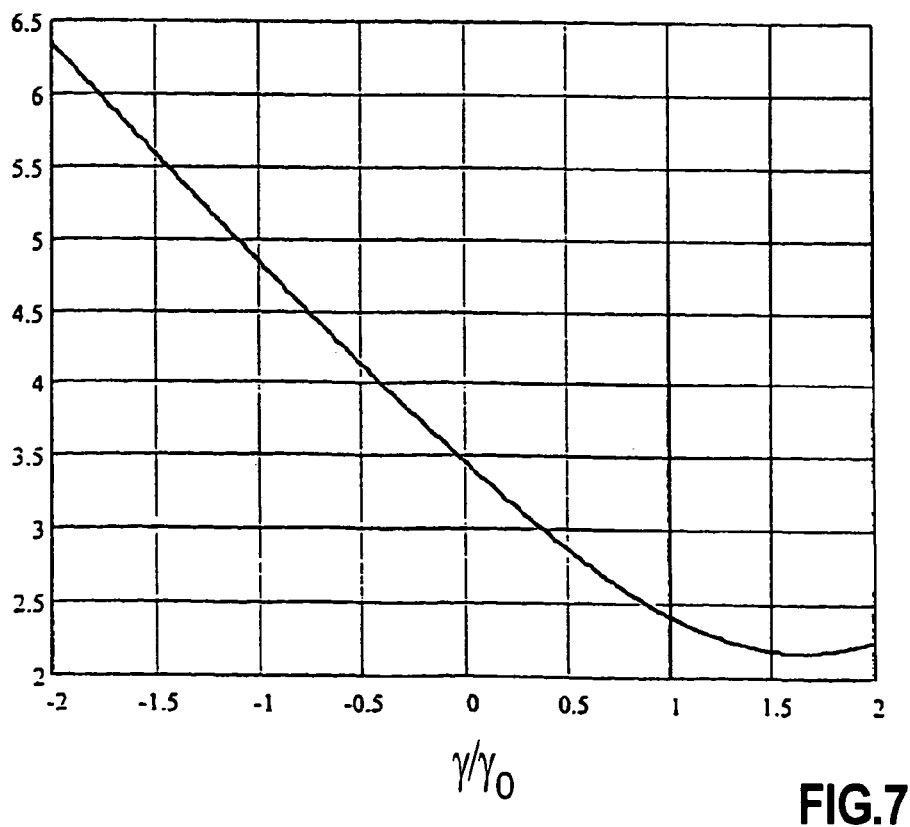
FIG. 7 shows the square roots of the square averages of the distances of all points of the spiral segment under consideration from the image plane measured in the direction of the z-axis, the square root being referenced to the width S of a detector row and being entered over the quotient $\gamma/\gamma_0$.

FIG. 7, based on FIG. 6 with the assumption that the spiral segment under consideration contributes its entire content to the respective image, shows the square root of the quadratic averages—referenced to the width S of a detector row—of the distances of all points of the spiral segment under consideration from the image plane measured in the direction of the z-axis, referred to below as SMSD (square root means square distance).

It is clear from FIG. 7 that SMSD decreases to 2.2 S by optimization of γ of 3.5 S for the case of an entirely uninclined image plane, i.e. γ=0. It is assumed that the improvement of the image quality that can be achieved according to U.S. Pat. No. 5,802,134 is to be attributed to this reduction of SMSD. For the pitch p under consideration, moreover, the value of the inclination angle γ for which SSMD is minimal differs only insignificantly from the value of $\gamma_0$ determined according to (8).

If instead of a single image that being reconstructed with respect to the entire spiral segment the number $n_{ima}$ of images with inclined image plane required as determined according to equation (12) is reconstructed, then a plurality $n_{ima}=2$ derives for the values M=12 and p=12 selected for the present example. This means that given an overall segment having the length $2\alpha_{max}=2\pi=360°$, two images with inclined image plane are reconstructed respectively for two spiral segments having the length 180° plus the cone angle, i.e., for example, the length 240°, that are offset by 120° relative to one another and thus cover the overall segment in common. The image planes of the images thereby exhibit different z-positions, and thus different tilt angles δ according to (11), namely $-\delta_{max}$ and $\delta_{max}$.

Figure 8:
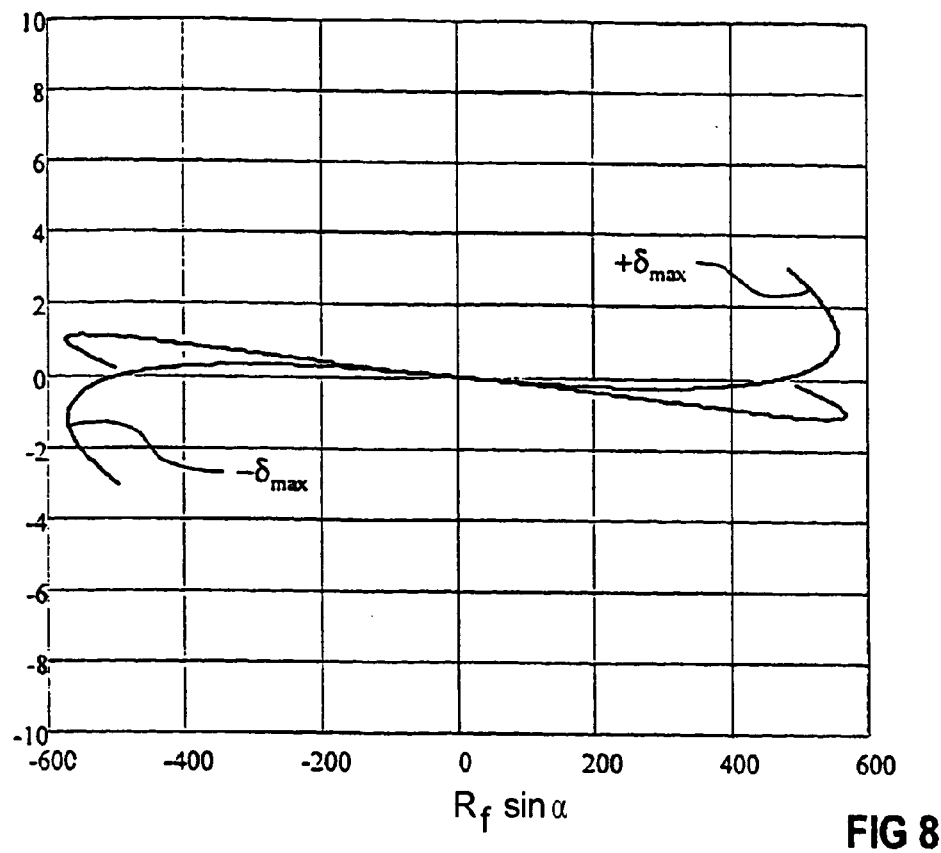
FIG. 8 shows the distances of all points of the spiral segment from the image planes inclined by $-\delta_{max}$ and $+\delta_{max}$ as well as by $\gamma_{min}$ of the two images belonging to this spiral segment over the sine of the projection angle a multiplied by the radius $R_f$, the distances being measured in the direction of the z-axis and being referenced to the width S of a row of detector elements for a spiral segment.

For one of the spiral segments having the length 240°, FIG. 8 shows the distances—referenced to the width S of a roll of detector elements and measured in the direction of the z-axis—of all points of this spiral segment from the image planes inclined by $-\delta_{max}$ or $+\delta_{max}$ as well as by $\gamma_{min}$ for the two images belonging to this spiral segment, over the sine of the projection angle a multiplied by the radius $R_f$. First, $\delta_{max}$ and $\gamma_0$ were determined on the basis of (8) and (10); for the purpose of optimization, a reiteration of the inclination angle γ on the basis of $\delta_{max}$ was then implemented, to which end SMSD was separately determined for both image planes of the spiral segment under consideration, then an overall SMSD was formed as square root of the separately determined SMSDs. Finally, the inclination angle γ was reiterated, which leads to $\gamma_{min}=1.26 \cdot \gamma_0$ and an SMSD of a total of 0.8 S.

Compared to the method disclosed in U.S. Pat. No. 5,802,134—tilt angle with δ=0 and reconstruction of a single image from the overall segment—this corresponds to a reduction of SMSD by a factor of more than 3 and promises a gain in image quality.

Figure 9:
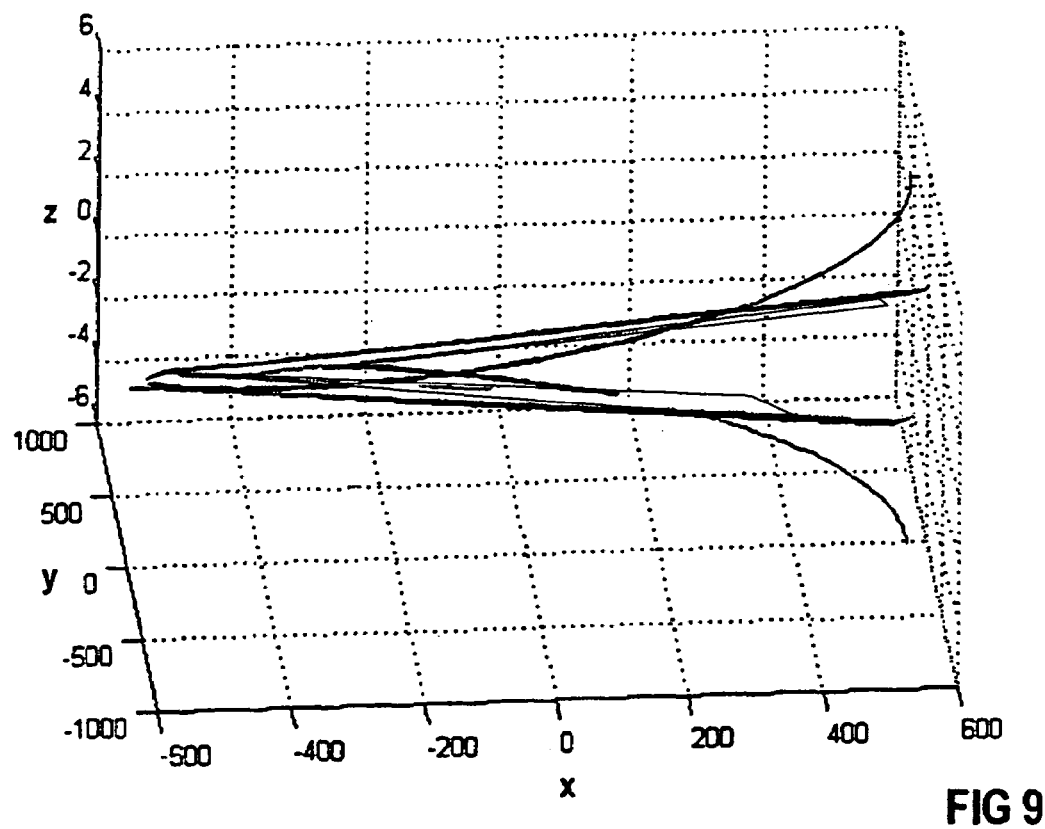
FIGS. 9 and 10 shows the image planes belonging to a spiral segment in a perspective illustration from different angles of view.
Figure 10:
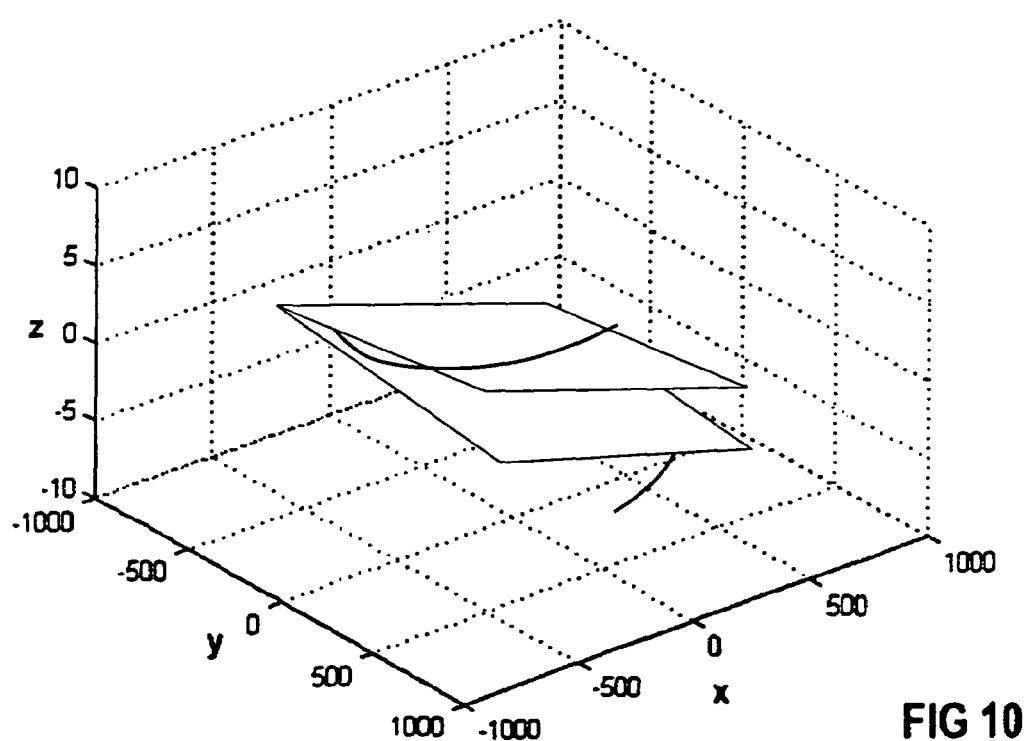

The image planes belonging to one of the two spiral segments of 240° (each are shown perspectively as examples in FIGS. 9 and 10 from different viewing angles). It can be particularly seen from FIG. 10 that the two inclined image planes, as mentioned, intersect in a straight line proceeding tangentially to the spiral.

Figure 11:
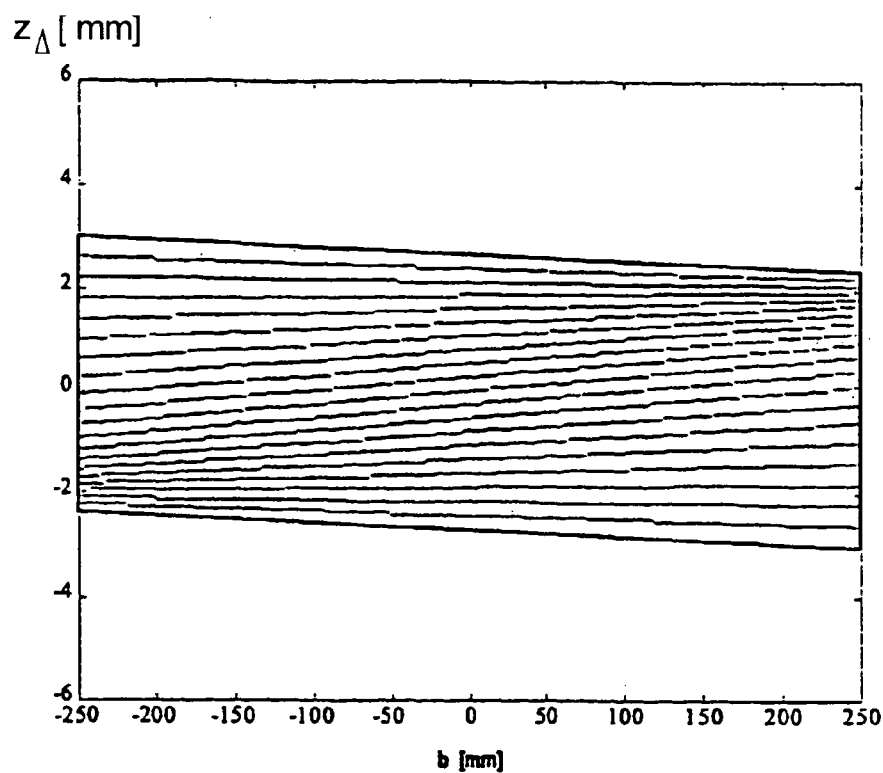
FIG. 11 illustrates the detector utilization, and thus dose utilization for a CT apparatus of the prior art on the basis of the virtual detector for M=12 and p=8.

The detector utilization, and thus the dose utilization, for the method disclosed in U.S. Pat. No. 5,802,134 is illustrated in FIG. 11 on the basis of the virtual detector for M=12 and p=8. The region limited with the bold face parallelogram-shaped line shows that region of the virtual detector area onto which the inclined image plane belonging to the spiral segment is projected during the movement of the focus along the spiral segment.

It is clear that large parts of the detector surface remain unused, and thus the detector utilization is also low. A theoretically optimum detector utilization and dose utilization is only possible for the maximum pitch $P_{max}=12$; detector utilization and dose utilization become poorer and poorer with decreasing pitch p.

Figure 12:
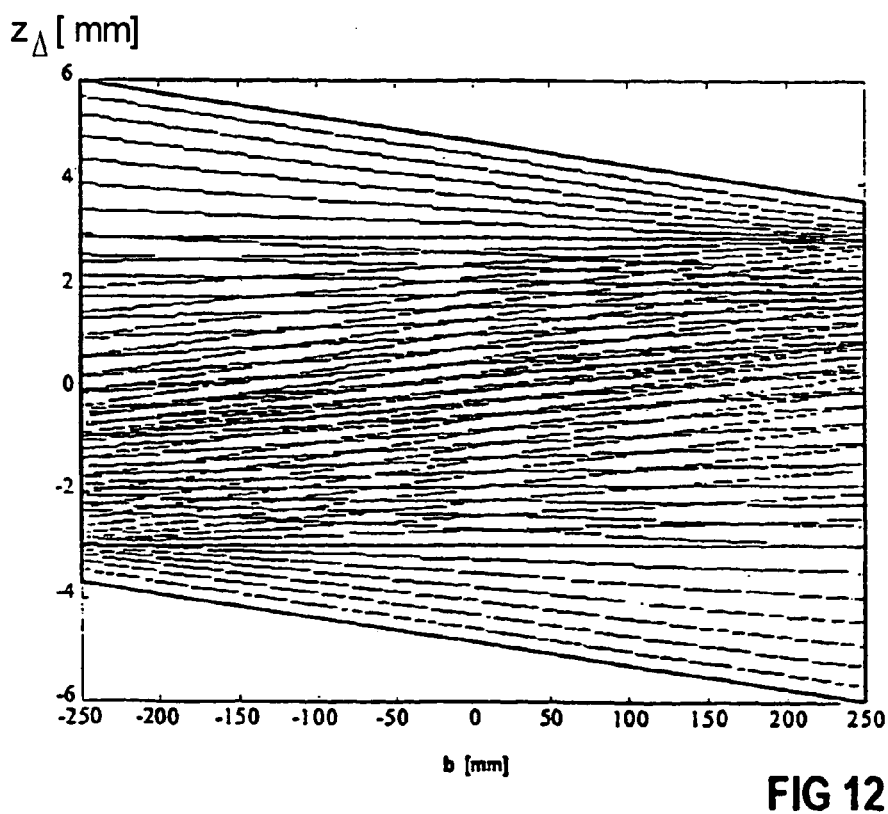
FIGS. 12 and 13 illustrate the detector utilization, and thus, dose utilization, for an inventive CT apparatus on the basis of the virtual detector, likewise for M=12 and p=8 or, respectively, for M=12 and p=12.
Figure 13:
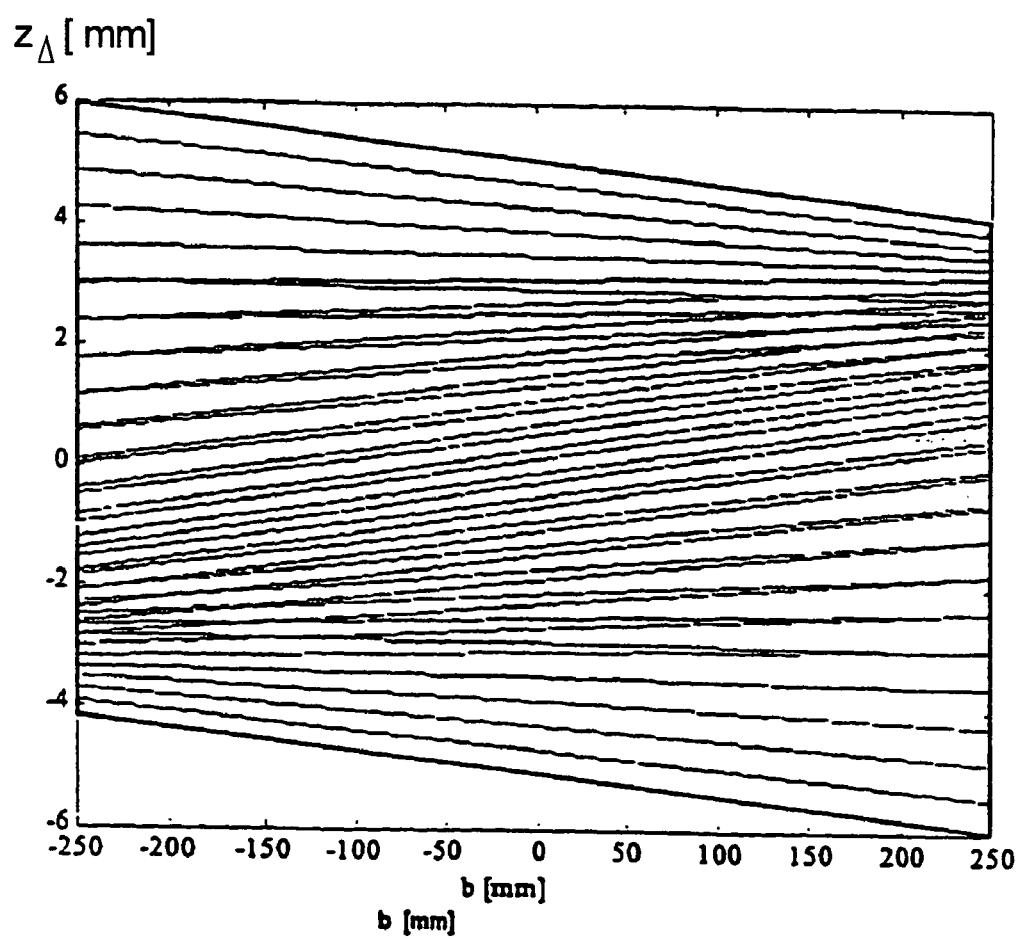

The detector utilization, and thus dose utilization for the invention is shown in FIG. 12 on the basis of the virtual detector, likewise for M=12 and p=8. The region bounded with the bold face parallelogram-shaped line thereby shows that region of the virtual detector surface onto which the $n_{ima}=3$ inclined image planes belonging to the spiral segment according to (12) are projected during the movement of the focus along the spiral segment.

It is clear that the majority of the virtual detector surface in the invention is utilized—only two small triangular regions remain unutilized—and that the dose utilization is correspondingly high.

As a comparison of FIG. 11 and FIG. 12 shows, only a slight dependency of the detector utilization and dose utilization on the pitch p exists in the case of the invention in practice, namely insofar as the two small unused triangular regions of virtual detector surface gradually increase with decreasing pitch p.

It is thus clear that, in contrast to the method disclosed in U.S. Pat. No. 5,802,134, the detector utilization, and thus the dose utilization, in the invention is largely independent of the pitch p and is nearly optimum.

The invention is also of significance for examinations of the heart.

Figure 14:
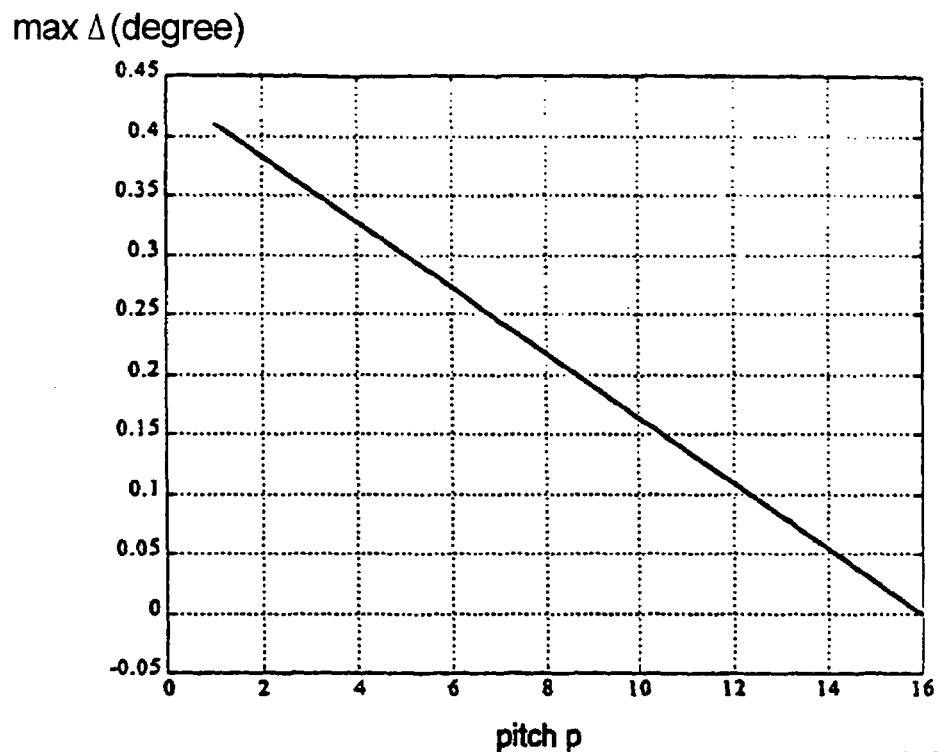
FIG. 14 shows the maximum tilt angle $\delta_{max}$ as a function of the pitch p for M=12.

FIG. 14 shows the maximum tilt angle $\delta_{max}$ determined according to (10) as function of the pitch p for a CT apparatus having M=12. It can be seen that the invention transforms into the algorithm disclosed in U.S. Pat. No. 5,802,134 for p=16, $\delta_{max}=0$. With $$\Delta z = R_f \tan \delta_{max} \qquad (13)$$

the inclination angle δ can be transformed into a z-shift of the corresponding image. This corresponds to a shift of the reference projection angle $\alpha_r$ $$\Delta \alpha = R_f \tan \delta_{max} \frac{2\pi}{pS} \qquad (14)$$

In accord therewith, images of spiral segments having a length of 240° can be calculated at an arbitrary z-position, these images being centered with respect to reference projection angles lying in a range of $[-\Delta\alpha, \Delta\alpha]$.

If one revolution of the gantry ensues in the time $T_{rot}$, this region corresponds to a time interval having the length $[-\Delta\alpha, \Delta\alpha]$.

$$\frac{T_{rot}}{2\pi}.$$

Figure 15:
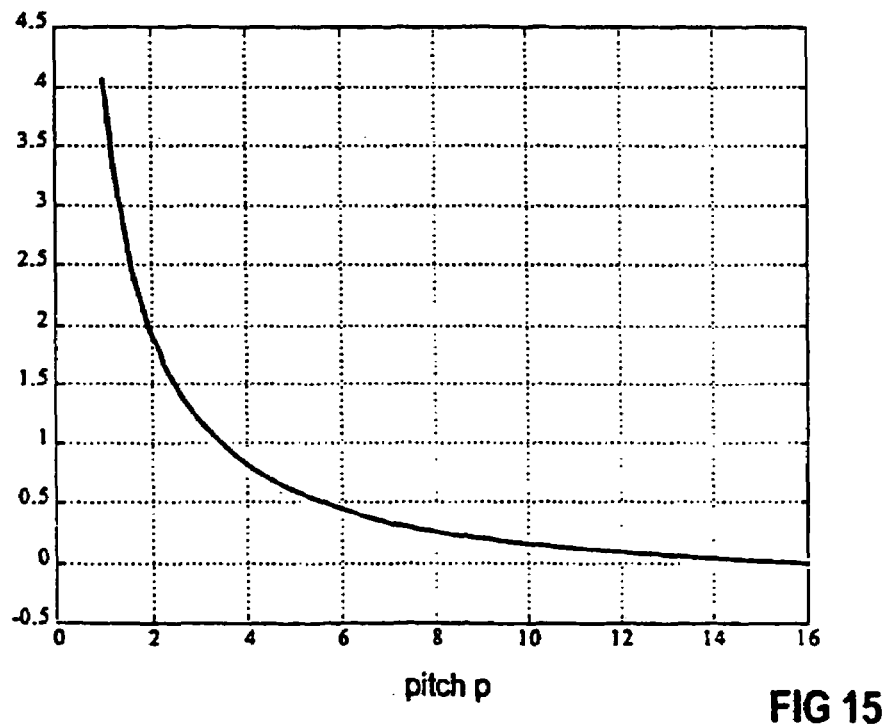
FIG. 15 shows the time interval covered for an arbitrary z-position as a function of the pitch p for $T_{rot}$=0.5 s.

The time interval covered for an arbitrary z-position is shown in FIG. 15 as function of the pitch p for $T_{rot}=0.5$ s.

If the totality of a spiral segment having the length 240° must be "forced" to fit onto the virtual detector surface, a maximum pitch of p=3 is available in order to cover a time interval of one second, which corresponds to a complete heart cycle given a pulse rate of 60 beats per minute (60 bpm).

Figure 16:
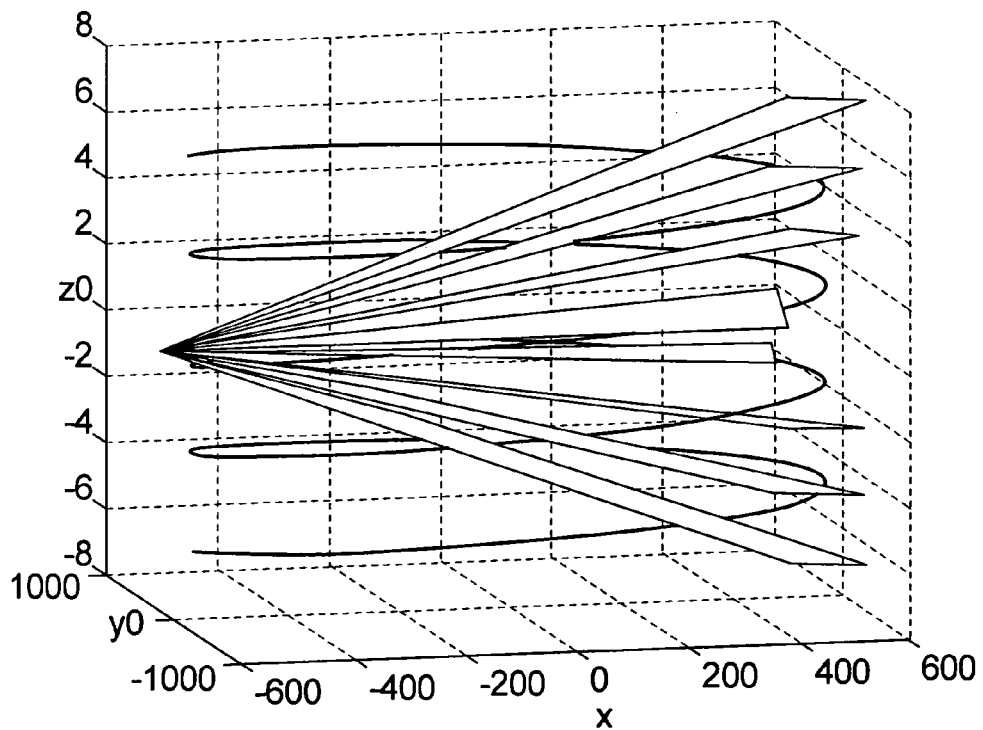
FIG. 16 shows the image planes of images that are acquired for the same reference projection angle $\alpha_r$, i.e. from the same heart cycle, namely for M=12, p=3.

The image planes of the images that are acquired for the same reference projection angle $\alpha_r$, i.e. from the same heart cycle, are illustrated in FIG. 16. A reformatting is required in order to obtain transverse tomograms.

As mentioned, a reformatting is required in order to obtain transverse tomograms, this not being required with a conventional CT apparatus.

Currently available multi-slice CT apparatus have a few rows of detector elements, for example four, available. The slanting beam course of the x-ray can be left out of consideration for this number of rows. Conventional algorithms therefore were expanded for such CT apparatus for the reconstruction of transverse tomograms from spiral data. After the implementation of a spiral weighting with a suitable weighting function for determining the reconstruction slice thickness, a single radiata set is present from which a transverse tomogram is reconstructed with a convolution—back-projection algorithm. The reconstruction slice thickness, i.e. the thickness of the slice of the examination subject acquired in the reconstructed transverse tomogram, is determined by the selection of the width of the weighting function employed in the spiral weighting. A modification of the reconstruction layer thickness is only possible on the basis of a renewed reconstruction with a modified weighting function.

The inventive procedure is especially suited for a CT apparatus that do not have an excessively great number of rows ($M \leq 40$). In accordance with the invention, an adaptation to the oblique beam course of the x-radiation ensues in the reconstruction by, as already explained, images being reconstructed for image planes that have their slope adapted to the spiral-like scan geometry. As a consequence of the inclination of the image planes, a recalculation of these images referred to below as reformatting is required after the reconstruction, set images having image planes inclined relative to the system axis in transverse tomograms. If this is not carried out, then geometrical distortion must be expected, particularly in secondary views of a reconstructed image volume (for example, sagittal or coronal).

The reformatting occurs using interpolation functions with selectable width, as a result whereof the slice sensitivity profile and the image noise in the resulting transverse tomogram can be influence.

It is advantageous that the definition of the desired reconstruction slice thickness ensues retrospectively during the course of the reformatting.

The number of images with inclined image plane required for the reformatting to be implemented for the acquisition of a transverse tomogram at the z-position $z=z_R$ is obtained in the following way:

at the edge of the object cylinder parameterized by (x, y)=($R_M \cos(\phi)$, $R_M \sin(\phi)$), the distance $\Delta z_R$ of an image plane inclined by the inclination angle and the tilt angle with the normal vector $$\bar{n}(\gamma, \delta) = \begin{pmatrix} \sin\delta \\ -\cos\delta\sin\gamma \\ \cos\delta\cos\gamma \end{pmatrix}$$

and with the zero point in the point ($-R_f$, 0, $z_R$) is obtained by introducing (x, y, $\Delta z_R$) is introduced into the plane equation $$\bar{n}(\delta, \gamma) \cdot \bar{x} = 0$$

It then follows that:

$$\Delta z_R = -\frac{\tan(\delta)}{\cos(\gamma)} \cdot (-R_f + R_M \cdot \cos(\Phi)) + \tan(\gamma) \cdot R_M \cdot \sin(\Phi). \quad (15)$$

For the reformatting of a transverse tomogram with the image plane in $z_R$, accordingly, all images with inclined image plane reconstructed in the interval $$[((z_R - sup_\Phi \Delta z_R(\Phi, \delta))) \cdot ((z_R + sup_\Phi \Delta z_R(\Phi, \delta)))] \quad (16)$$

must be available, i.e., be stored in the memory 14.

When an interpolation function whose length $z^*$ exceeds the limit values set by the above interval is employed in the reformatting, then the plurality of reconstructed images with inclined image plane required for the reformatting is determined by the length of the interpolation filter.

In the general case, $$N_M = 2 \cdot \max(z^*, sup_\phi \Delta z_R) / S \cdot N_S \quad (17)$$

applies for $N_M$ reconstructed images with inclined image plane required for the reformatting of a transverse tomogram. $N_S$ is the number of images with inclined image plane reconstructed per width S of a row of detector elements.

For a detector array with 16 rows of detector elements, for a pitch of p=16 and $N_S$=4 images with inclined image plane reconstructed per width S, for example, $N_M$=10 is obtained the number of the reconstructed images with inclined image plane required for reformatting a transverse tomogram, namely with the pre-condition of employing a triangular interpolation function of the half-width value S.

As a consequence of the retrospective definition of the reconstruction slice thickness of a desired transverse tomogram, the reconstruction of the images with inclined image plane preferably ensues by selecting a correspondingly narrow weighting function in the spiral reconstruction with the smallest possible reconstruction slice thickness. This assures utmost sharpness in the z-direction not only for the images with inclined image plane but also for the transverse tomogram obtained by the reformatting.

The following are further advantages of the described reformatting in addition to this advantage:

The reconstruction slice thickness can be retrospectively selected without a renewed reconstruction being required;

The reconstruction slice thickness is freely selectable; and

A number of suitable interpolation functions of freely selectable width is available for the reformatting.

Figure 17:
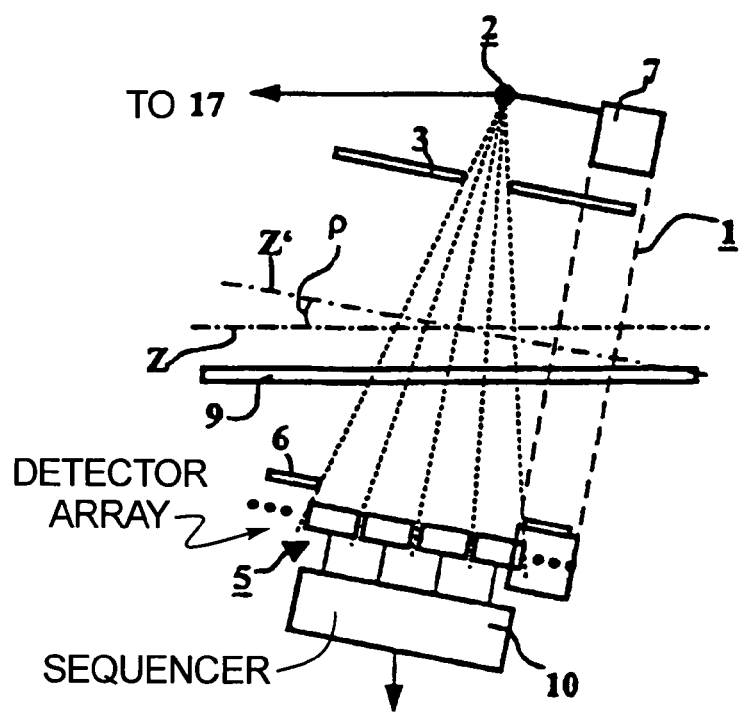
FIG. 17 shows the inventive CT apparatus in an operating mode with the gantry inclined relative to the system axis, in a presentation analogous to FIG. 4.
Figure 5:
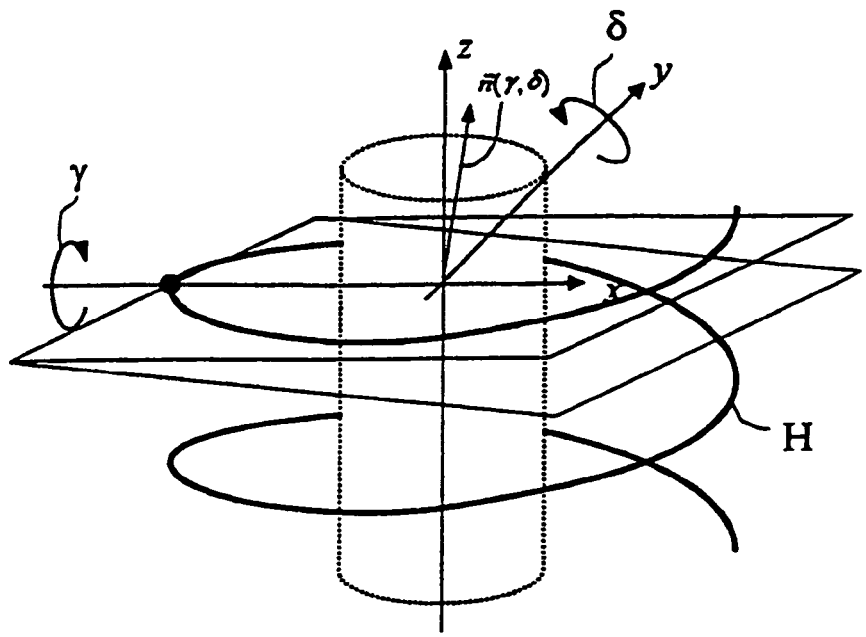
FIG. 5 is a diagram illustrating the geometry of the inventive method in a former presentation analogous to FIGS. 1 and 2.
Figure 18:
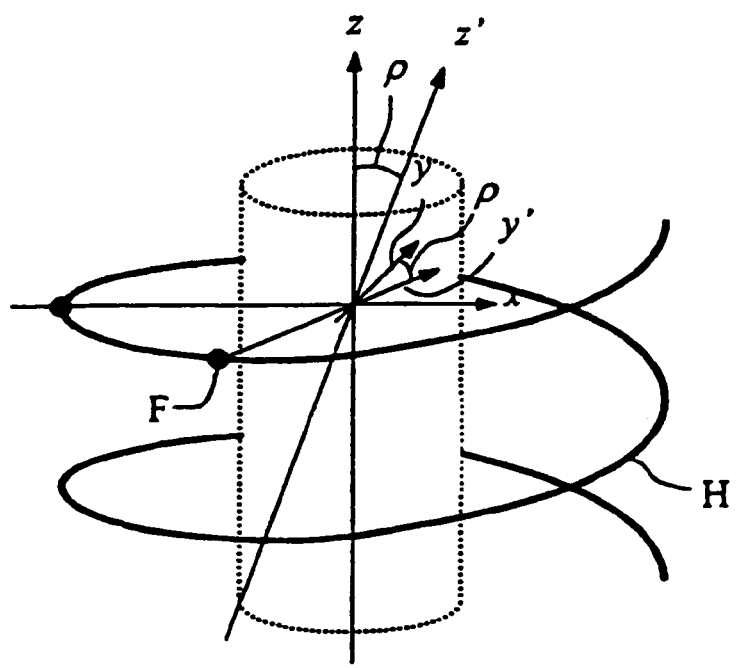
FIG. 18 illustrates the geometry of the inventive CT apparatus for the operating mode according to FIG. 17, in a presentation analogous to FIG. 1.

When, as in the operating mode with inclined gantry 7 illustrated in FIG. 17, the rotational axis Z' around which the focus F rotates around the symmetry axis z is not identical to the system axis Z but intersects this the gantry angle $\rho$, then the geometry according to FIG. 5 yields a coordinate system tilted according to FIG. 18 with the Z'-axis corresponding to the center axis of the spiral path H that is tilted by the gantry angle $\rho$ relative to the Z-axis (and the z-axis), the y'-axis that is likewise tilted by the gantry angle $\rho$ compared to the y-axis, and the x-axis which is retained unmodified.

In this coordinate system, the following applies to the spiral path H:

$$\overline{x}_f \cdot = \begin{pmatrix} -R_f\cos\alpha \\ -R_f\sin\alpha + Sp\dfrac{\alpha\sin\rho}{2\pi} \\ Sp\dfrac{\alpha\cos\rho}{2\pi} \end{pmatrix} \quad (18)$$

The procedure described above for determining the maximum tilt angle $\delta_{max}$ can be transferred to the case of the tilted gantry, whereby the following applies instead of Equation (7):

$$z'_{Det}(b) = z'(b) - Sp\dfrac{\alpha\cos\rho}{2\pi} = \quad (19)$$
$$-R_f\dfrac{\tan\delta}{\cos\gamma} - Sp\dfrac{\alpha\cos\alpha}{2\pi} - b\left(\sin\alpha\dfrac{\tan\delta}{\cos\gamma} + \cos\alpha\tan\gamma\right),$$

from which the following derives for $b=\pm RFOV$:

$$z'_{Det}(b=\pm RFOV) = \pm\dfrac{SM}{2}\sqrt{1-\left(\dfrac{b}{R_f}\right)^2} + \alpha\sin\dfrac{b}{R_f}Sp\dfrac{\cos\alpha}{2\pi} \quad (20)$$

ver, the inclination angle $\gamma'$ in the coordinate system (x, y', z') for the case of the inclined gantry then must be introduced into the definition equation for the maximum tilt angle $\delta_{max}$, i.e. into equation (10).

The following applies for the inclination angle $\gamma'$ in the case of the inclined gantry:

$$\tan\gamma = \quad (21)$$
$$\partial z \dfrac{\partial z'}{\partial s} = \dfrac{\partial z'}{\partial \alpha} \cdot \dfrac{\partial \alpha}{\partial s} = \dfrac{Sp\cdot\cos\rho}{\sqrt{4\pi^2\cdot R_f + S^2p^2 + 4\pi\cdot R_f\cos\alpha\sin\rho\cdot Sp}}$$

and $$\gamma' = \arctan\dfrac{Sp\cdot\cos\rho}{\sqrt{4\pi^2\cdot R_f + S^2p^2 + 4\pi\cdot R_f\cos\alpha\sin\rho\cdot Sp}}$$

whereby s is the arc length of the spiral path H for the spiral segment respectively under consideration.

Figure 19:
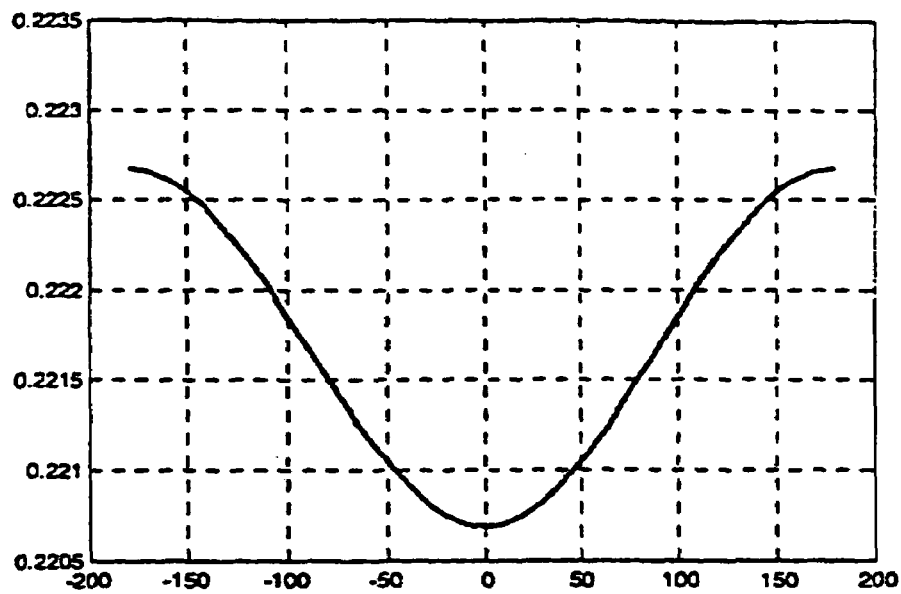
FIG. 19 shows the curve of the inclination angle γ' for the case of the tilted gantry dependent on the reference projection angle $\alpha_r$, namely for M=16, p=16 and a gantry angle of δ=30°.

As FIG. 19 shows, the inclination angle $\gamma'$ for the case of the tilted gantry is nearly independent of the reference projection angle $\alpha_r$. FIG. 19 shows the situation for a number of rows M=16, a pitch p=16 and a gantry angle of $\rho=30°$.

Figure 20:
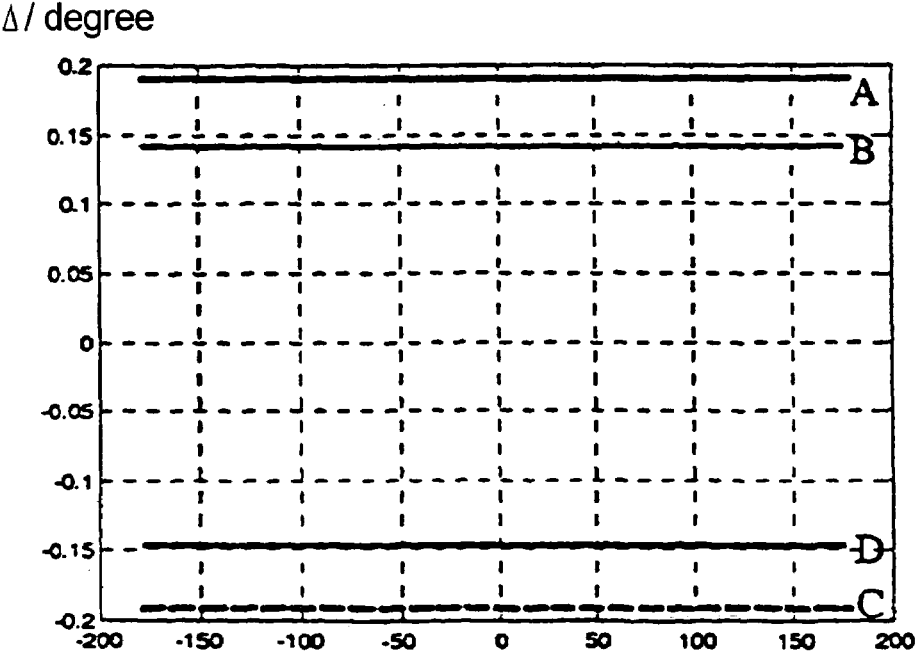
FIG. 20 shows the curve of the maximum tilt angle $\delta_{max}$ for the case of the tilted gantry dependent on the reference projection angle $\alpha_r$ for M=16, p=16, and, namely, for ρ=30° as well as ρ=0° and ±RFOV.

As can be seen from FIG. 20, the maximum tilt angle $\delta_{max}$ is also nearly independent of the reference projection angle $\alpha_r$, whereby FIG. 20 also shows the situation for the number of rows M=16, the pitch p=16 and the gantry angle $\rho=30°$. The curve of the maximum tilt angle $\delta_{max}$ for +RFOV and $\rho=30°$ is indicated with 'A', whereas C indicates the curve of the maximum inclination angle for −RFOV and $\rho=30°$.

For comparison, the corresponding curves of the maximum tilt angle $\delta_{max}$ are entered in FIG. 20 for a gantry angle of $\rho=0°$, whereby B is valid for +RFOV and $\rho=0°$ applies, whereas D is valid for −RFOV and $\rho=0°$ applies.

Figure 21:
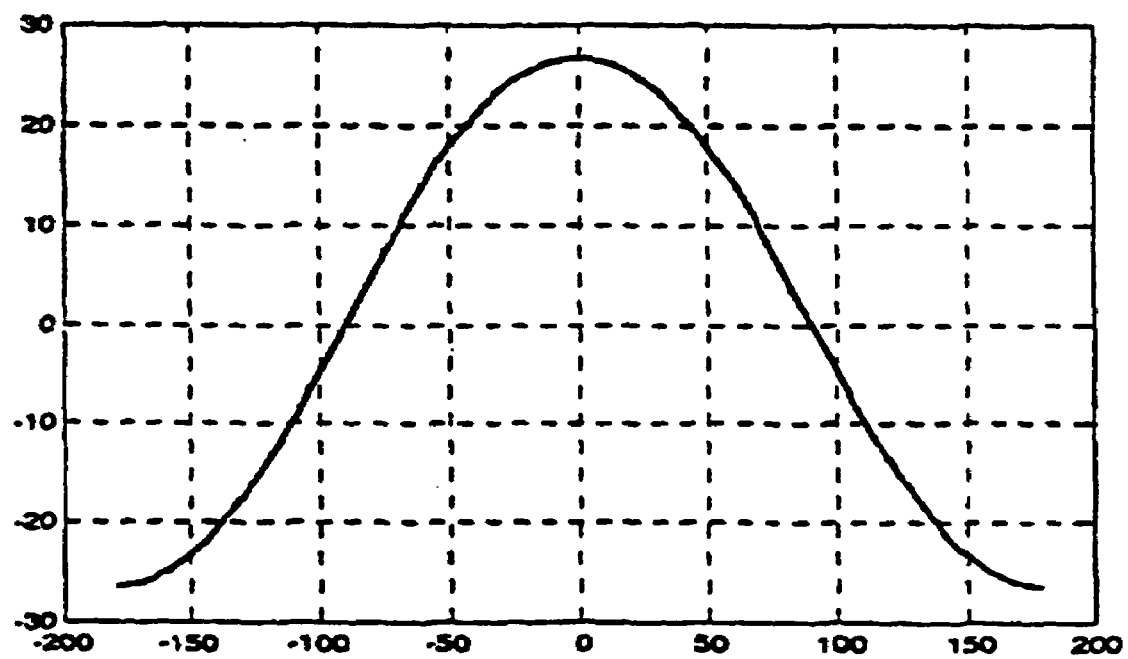
FIG. 21 shows a CT apparatus of the prior art in a presentation analogous to FIG. 19.

For illustrating the effect of the invention, FIG. 21—analogous to FIG. 19—shows the curve of the inclination angle $\gamma$ as a function of the reference projection angle, likewise for a number of rows of M=16, a pitch p=16 and a gantry angle of $\rho=30°$ for the method disclosed in U.S. Pat. No. 5,802,134. It clear that there is a pronounced dependency of the inclination angle $\gamma$ on the reference projection angle $\alpha_r$ here.

FIGS. 19 through 21, moreover, each show a full revolution (360°) of the focus F.

For a given magnitude of the maximum value of the tilt angle $|\delta_{max}|$ that, for example, is acquired from (10) on the basis of the criteria according to (21) from the slope of the spiral path H, there is also the possibility in the case of an inclined gantry to determine the appertaining optimum value for the inclination angle $\gamma'$ such that an error criterion, for example minimum average of the distances of all points of the spiral segment from the image plane measured in z-direction, is met.

In the exemplary embodiment, the structure of the image computer 11 is described in a way as though the pre-processing unit 12 and the reconstruction unit 13 were hardware components. This can in fact be the case. As a rule, however, these components are realized by software modules that run on a universal computer provided with the required interfaces and that, deviating from FIG. 1, can also assume the function of the control unit 18.

In the described exemplary embodiment, the CT apparatus has a detector array 5 with rows each having a width measured in the z-direction of identical size which, for example, amounts to 1 mm. A detector array alternatively can be used within the framework of the invention whose rows have different widths. For example, two inner rows can be provided each having a width of 1 mm, with respective rows each having a width of 2 mm provided at opposite sides of the inner rows.

In the described exemplary embodiments, the relative movement between the measuring unit 1 and the support mechanism 9 is produced by displaying the support mechanism 9. However, there is also the possibility within the framework of the invention to leave the support mechanism 9 stationary and to instead displace the measuring unit 1. Within the framework of the invention, moreover, there is also the possibility of generating the required relative motion by displacing both the measuring unit 1 and the bearing mechanism 9.

A CT apparatus of the third generation is employed in conjunction with the above-described exemplary embodiments, i.e. the x-ray source and the detector array are displaced in common around the system axis during the image generation. The invention, however, also can be employed in conjunction with a CT apparatus of the fourth generation wherein only the x-ray source is displaced around the system axis and interacts with a stationary detector ring, which is a planar array of detector elements.

The inventive method also can be employed in a CT apparatus of the fifth generation, i.e. a CT apparatus wherein x-rays does not emanate from a single focus but from a multiple of foci of one or more x-ray sources displaced around the system axis insofar, with the detector array being a planar array of detector elements.

The CT apparatus employed in conjunction with the above-described exemplary embodiments has a detector array with detector elements arranged in the fashion of an orthogonal matrix. The invention, however, also can be employed in conjunction with CT apparatus with a detector array having detector elements arranged in some other way than a planar array.

The above-described exemplary embodiments relate to the medical application of the inventive method. The invention, however, also can be employed beyond medicine, for example in baggage inspection or in examining materials.

Although modifications and changes may be suggested by those skilled in the art, it is in the intention of the inventors to embody within the patent warranted hereon all changes and modifications as reasonably and property come within the scope of their contribution to the art.

We claim as our invention:

1. A method for computed tomography comprising the steps of:
   a) scanning a subject with a conical radiation beam emanating from a focus of a radiation source and detecting radiation attenuated by said subject with a matrix detector array while moving the focus relative to the subject on a spiral path around a system axis, said detector array supplying output data corresponding to the detected radiation; and
   b) reconstructing images having an inclined image plane from output data supplied during the movement of the focus on a spiral segment, the image planes of said images being inclined by an inclination angle $\gamma$ around a first axis intersecting the system axis at a right angle and also being inclined by a tilt angle $\delta$ with respect to the system axis around a second axis that intersects the first axis and the system axis at a right angle.

2. A method as claimed in claim 1, wherein said focus moves around a z-axis comprising reconstructing said images with inclined image plane for a plurality $n_{ima}$ of successive spiral segments, the inclined image planes exhibiting a same z-position $z_{ima}$ on the z-axis, and immediately succeeding spiral segments being offset by at most 180° relative to one another and yielding an overall spiral segment having a length $[-\alpha_{max}, +\alpha_{max}]$ wherein $\alpha_{max}=M\pi/p$ and M is a plurality of detector rows in said detector and p is a pitch of said spiral path.

3. A method as claimed in claim 1, wherein said focus moves around a z-axis on said signal path and wherein each spiral segment has a length of 180° plus a cone angle of said radiation beam, and comprising reconstructing said images with inclined image plane for a plurality $n_{ima}$ of successive spiral segments, the inclined image planes exhibiting different positions $z_{ima}$ on the z-axis.

4. A method as claimed in claim 3, wherein the plurality of inclined image planes intersect in a straight line proceeding tangentially to the spiral path.

5. A method as claimed in claim 3, wherein said array is composed of M rows of adjacent rows extending transversely to the system axis and each having a width S and wherein for extreme values $+\delta_{max}$ and $-\delta_{max}$ of the tilt angle $\delta$ of the inclined image planes belonging to a spiral segment:

$$\pm\delta_{max} = \arctan\left(\frac{-\frac{SM}{2} + Sp\frac{\alpha_l}{2\pi} \pm RFOV\cos\alpha_l \tan\gamma_0}{-\frac{R_f}{\cos\gamma_0} - (\pm RFOV)\frac{\sin\alpha_l}{\cos\gamma_0}}\right)$$

wherein ±RFOV is a region of rows of said detector array, relative to a center of said detector array along the system axis, corresponding to a region of said subject covered by said radiation, $\gamma_0$ is a value of the inclination angle $\gamma$ according to $$\gamma_0 = \tan\left(\frac{-Sp\hat{\alpha}}{2\pi R_f \sin\hat{\alpha}}\right)$$

for the tilt angle $\delta=0$, wherein $R_F$ is a position of the focus in the image plane and a is an angle at which the spiral path penetrates the image plane.

6. A method as claimed in claim 5, wherein the focus rotates around a rotational axis that coincides with the system axis.

7. A method as claimed in claim 5, comprising rotating the focus around a symmetry axis that does not coincide with the system axis and which intersects the system axis at a gantry angle $\rho$, and wherein:

$$\gamma' = \arctan\frac{Sp\cdot\cos\rho}{\sqrt{4\pi^2\cdot R_f + S^2p^2 + 4\pi\cdot R_f\cos\alpha\sin\rho\cdot Sp}}.$$

8. A method as claimed in claim 5 comprising setting an optimum value $\gamma_{min}$ of the inclination angle $\gamma$ for a magnitude of the maximum value of the tilt angle $|\delta_{max}|$ so that an error criterion is satisfied.

9. A method as claimed in claim 3, wherein the detector array comprises M adjacent rows extending transversely to the system axis, each row having a width S, and wherein said spiral path has a pitch p, and comprising selecting a plurality $n_{ima}$ of the inclined image planes for which images having inclined image plane are generated for each spiral segment according to:

$$n_{ima} = \text{floor}\left[\frac{SM}{P}\right].$$

10. A method as claimed in claim 9, comprising selecting respective tilt angles $\delta(i)$ of the inclined image planes $n_{ima}$ according to $$\delta(i) = \delta_{max}\frac{2i-(n_{ima}-1)}{n_{ima}-1}.$$

11. A method as claimed in claim 1, comprising combining at least some of the plurality of images having inclined image plane to form a transverse tomogram having a transverse slice intersecting the system axis at a right angle.

12. A method as claimed in claim 11, comprising combining the plurality of images with inclined image plane to form said transverse tomogram by interpolation.

13. A method as claimed in claim 11, comprising combining the plurality of images with inclined image plane to form said transverse tomogram by forming an average.

14. A method as claimed in claim 13, comprising combining the plurality of images with inclined image plane to form said transverse tomogram by weighted averaging.

15. A method as claimed in claim 11, comprising selecting images among the plurality of images with inclined image plane for combining for generating said transverse tomogram according to a desired slice thickness of the transverse slice.

16. A method as claimed in claim 15, comprising selecting said images among the images with inclined image plane having a smallest possible slice thickness.

17. A method as claimed in claim 15, comprising selecting said images among the plurality of images having inclined image plane for combining for generating said transverse tomogram according to $$N_M = 2 \cdot \max(z^*, \sup_\phi \Delta z_R)/S \cdot N_S.$$

18. A computed tomography apparatus for computed tomography comprising the steps of:
a scanner having a radiation source and a matrix detector scanning a subject with a conical radiation beam emanating from a focus of said radiation source and detecting radiation attenuated by said subject with said detector array while moving the focus relative to the subject on a spiral path around a system axis, said detector array supplying output data corresponding to the detected radiation; and
a computer supplied with said output data for reconstructing images having an inclined image plane from said output data supplied during the movement of the focus on a spiral segment, the image planes of said images being inclined by an inclination angle $\gamma$ around a first axis intersecting the system axis at a right angle and also being inclined by a tilt angle $\delta$ with respect to the system axis around a second axis that intersects the first axis and the system axis at a right angle.

19. A computed tomography apparatus as claimed in claim 18, wherein, in said scanner, said focus moves around a z-axis comprising reconstructing said images with inclined image plane for a plurality $n_{ima}$ of successive spiral segments, the inclined image planes exhibiting a same z-position $z_{ima}$ on the z-axis, and immediately succeeding spiral segments being offset by at most 180° relative to one another and yielding an overall spiral segment having a length $[-\alpha_{max}, +\alpha_{max}]$, wherein $\alpha_{max} = M\pi/p$ and M is a plurality of detector rows in said detector and p is a pitch of said spiral path.

20. A computed tomography apparatus as claimed in claim 18, wherein, in said scanner, said focus moves around a z-axis on said signal path and wherein each spiral segment has a length of 180° plus a cone angle of said radiation beam, and wherein said computer reconstructs said images with inclined image plane for a plurality $n_{ima}$ of successive spiral segments, the inclined image planes exhibiting different positions $z_{ima}$ on the z-axis.

21. A computed tomography apparatus as claimed in claim 20, wherein said scanner obtains the plurality of images with inclined image planes so that the inclined image planes intersect in a straight line proceeding tangentially to the spiral path.

22. A computed tomography apparatus as claimed in claim 20, wherein said array is composed of M rows of adjacent rows extending transversely to the system axis and each having a width S and wherein for extreme values $+\delta_{max}$ and $-\delta_{max}$ of the tilt angle $\delta$ of the inclined image planes belonging to a spiral segment:

$$\pm \delta_{max} = \arctan \left( \frac{-\frac{SM}{2} + Sp\frac{\alpha_i}{2\pi} \pm RFOV\cos\alpha_i \tan\gamma_0}{-\frac{R_f}{\cos\gamma_0} - (\pm RFOV)\frac{\sin\alpha_i}{\cos\gamma_0}} \right)$$

wherein ±RFOV is a region of rows of said detector array, relative to a center of said detector array along the system axis, corresponding to a region of said subject covered by said radiation, $\delta_0$ is a value of the inclination angle $\gamma$ according to $$\gamma_0 = \tan\left( \frac{-Sp\hat{\alpha}}{2\pi R_f \sin\hat{\alpha}} \right)$$

for the tile angle $\delta=0$ wherein $R_F$ is a position of the focus in the image plane and $\alpha$ is an angle at which the spiral path penetrates the image plane.

23. A computed tomography apparatus as claimed in claim 22, wherein the scanner rotates the focus around a rotational axis that coincides with the system axis.

24. A computed tomography apparatus as claimed in claim 22, wherein the scanner rotates the focus around a symmetry axis that does not coincide with the system axis and which intersects the system axis at a gantry angle $\rho$, and wherein:

$$\gamma' = \arctan \frac{Sp \cdot \cos\rho}{\sqrt{4\pi^2 \cdot R_f + S^2 p^2 + 4\pi \cdot R_f \cos\alpha \sin\rho \cdot Sp}}.$$

25. A computed tomography apparatus as claimed in claim 22 comprising an input unit connected to said computer for setting an optimum value $\gamma_{min}$ of the inclination angle $\gamma$ for a magnitude of the maximum value of the tilt angle $|\delta_{max}|$ so that an error criterion is satisfied.

26. A computed tomography apparatus as claimed in claim 20, wherein the detector array comprises M adjacent rows extending transversely to the system axis, each row having a width S, and wherein said spiral path has a pitch p, and wherein said computer selects a plurality $n_{ima}$ of the inclined image planes for which images having inclined image plane are generated for each spiral segment according to:

$$n_{ima} = \mathrm{floor}\left[\frac{SM}{P}\right].$$

27. A computed tomography apparatus as claimed in claim 26, wherein said computer selects respective tilt angles $\delta(i)$ of the inclined image planes according to $$\delta(i) = \delta_{max} \frac{2i - (n_{ima} - 1)}{n_{ima} - 1}.$$

28. A computed tomography apparatus as claimed in claim 18, wherein said computer combines at least some of the plurality of images having inclined image plane to form a transverse tomogram having a transverse slice intersecting the system axis at a right angle.

29. A computed tomography apparatus as claimed in claim 28, wherein said computer combines the plurality of images with inclined image plane to form said transverse tomogram by interpolation.

30. A computed tomography apparatus as claimed in claim 28, wherein said computer combines the plurality of images with inclined image plane to form said transverse tomogram by forming an average.

31. A computed tomography apparatus as claimed in claim 30, wherein said computer combines the plurality of images with inclined image plane to form said transverse tomogram by weighted averaging.

32. A computed tomography apparatus as claimed in claim 28, wherein said computer selects images among the plurality of images with inclined image plane for combining for generating said transverse tomogram according to a desired slice thickness of the transverse slice.

33. A computed tomography apparatus as claimed in claim 32, wherein said computer selects said images among the images with inclined image plane having a smallest possible slice thickness.

34. A computed tomography apparatus as claimed in claim 32, wherein said computer selects said images among the plurality of images having inclined image plane for combining for generating said transverse tomogram according to $$N_M = 2 \cdot \max(z^*, \sup\phi \Delta z_R)/S \cdot N_S.$$

* * * * *